(12) United States Patent
Kaufman

(10) Patent No.: US 6,873,677 B2
(45) Date of Patent: Mar. 29, 2005

(54) METHOD AND DEVICE FOR IMPROVING TIME RESOLUTION OF AN IMAGING DEVICE

(75) Inventor: Leon Kaufman, 161-4th Ave., San Francisco, CA (US) 94118

(73) Assignees: Leon Kaufman, Palo Alto, CA (US); Joel Blank, Palo Alto, CA (US)

( * ) Notice: Subject to any disclaimer, the term of this patent is extended or adjusted under 35 U.S.C. 154(b) by 154 days.

(21) Appl. No.: 10/419,710

(22) Filed: Apr. 18, 2003

(65) Prior Publication Data

US 2004/0208276 A1 Oct. 21, 2004

(51) Int. Cl.$^7$ ................................. A61B 6/03
(52) U.S. Cl. ........................ 378/4; 378/9; 378/10; 378/15; 378/901
(58) Field of Search ............... 378/4, 8, 9, 10, 378/15, 19, 901

(56) References Cited

U.S. PATENT DOCUMENTS

| | | | |
|---|---|---|---|
| 4,138,721 A | 2/1979 | Boyd | |
| 4,196,352 A | 4/1980 | Berninger et al. | |
| 4,352,021 A | 9/1982 | Boyd et al. | |
| 4,991,190 A | 2/1991 | Mori | |
| 5,053,958 A | 10/1991 | Tam | |
| 5,604,778 A | 2/1997 | Polacin et al. | |
| 5,966,422 A | 10/1999 | Dafni et al. | |
| 6,327,326 B1 | 12/2001 | Flohr et al. | |
| 2003/0215120 A1 * | 11/2003 | Uppaluri et al. | ............ 382/128 |

OTHER PUBLICATIONS

Rueckert D., et al., "Nonrigid Registration Using Free–Form Deformations: Application to Breast MR Images," *IEEE Trans Medical Imaging*, 1999, Aug.;18, (8):712–21.

Rueckert D., et al., Non–Rigid Registration of Breast MR Images using Mutual Information, *CRC Clinical Magnetic Resonance Research Group*, Royal Marsden Hospital, Sutton SM2 5PT, UK, (date not given).

Sheehan F.H. et al, "Method for Three–Dimensional Data Registration from Disparate Imaging Modalities in the NOGA Myocardial Viability Trial," *IEEE Trans Medical Imaging* vol. 21, No. 10, Oct. 2002, pp. 1264–1270.

Faber T.I., et al., "Spatial and Temporal Registration of Cardiac Spect and MR Images: Methods and Evaluation," *Radiology* 1991 179: 857–861.

Dentor E.R., et al., "Comparison and Evaluation of Rigid, Affine, and Nonrigid Registration of Breast MR Images," *J Comput Assist Tomogr* Sep.–Oct. 1999; 23(5):800–5.

* cited by examiner

*Primary Examiner*—David V Bruce
(74) *Attorney, Agent, or Firm*—Townsend and Townsend and Crew LLP

(57) ABSTRACT

The present invention provides methods and devices which improve a time resolution of a scanner by segmenting the data and generating a plurality of low resolution images. The low resolution images may then be combined to reconstruct a full image of a slice of a target. Such a method improves the time resolution of the scanner while maintaining the radiation dosage and time of the scan.

39 Claims, 6 Drawing Sheets

METHOD AND DEVICE FOR IMPROVING TIME RESOLUTION OF AN IMAGING DEVICE

BACKGROUND OF THE INVENTION

The present invention is generally related to computed tomography (CT) and electron beam tomography (EBT) scanning devices and methods. More specifically, the present invention is related to improving a time resolution of a CT and EBT scanning device.

In an x-ray CT scanner, an x-ray tube is rotated around the body and transmits x-rays through the patient to a rotating detector array or fixed detector array. In this way multiple absorption rays of the patient are obtained. Many algorithms exist today to reconstruct the absorption values as an image that represents the local attenuation of x-rays of the body tissues of the patient that are imaged.

In a conventional mechanical CT scanner, the x ray tube output is generally fan-shaped, with a fan angle of approximately sixty degrees. Typically, the x-ray tube moves through a complete 360 degree rotation to obtain a full data set for a single tomograph. Reconstruction of the tomograph, however, can be reconstructed from a less than full attenuation data set (e.g., less than 360 degrees of rotation, e.g., 180 degrees plus the fan beam arc). Thus, if the tube gantry rotation time is 500 msec, the data needed to acquire an image will require over 333 msec of acquisition time. Unfortunately, an organ such as the heart, will typically have undergone half of its cyclical motion in that time, and the image will exhibit blur and motion artifacts.

In an EBT scanner, rather than a moving x-ray tube, the detectors are fixed and an x-ray beam is scanned or directed across a target tissue from different points of a tungsten target arc that is impinged upon by a steered beam of electrons. Mathematically, the reconstruction process is the generally the same for an EBT scanner as for a mechanical CT scanner, except that the electron beam can be scanned faster than an x-ray tube can be moved. Consequently, the imaging time of a patient is faster and is typically between approximately 50 msec to approximately 100 msec for each slice.

While EBT scanners are faster than mechanical CT scanners, EBT scanners still may not meet the requirements of processes that require better time resolution than can be provided by the conventional CT scanners and EBT scanners.

For the above reasons, what are needed are methods and devices that improve the time resolution of mechanical and electron beam CT scanners.

DESCRIPTION OF THE BACKGROUND ART

U.S. Pat. Nos. 5,966,422, 5,604,778, 4,991,190, and 4,196,352 provide scanner system that includes multiple x-ray sources. U.S. Pat. Nos. 4,138,721 and 5,053,958 describe limited angle image reconstruction.

BRIEF SUMMARY OF THE INVENTION

The present invention provides methods and devices for increasing a time resolution of mechanical CT scanners and EBT scanners without significantly affecting the radiation dosage to the patient or the cost of manufacturing the scanner.

The present invention improves a time resolution of a scanner by segmenting the attenuation data and creating a plurality of low resolution images with the segmented attenuation data. The plurality of low resolution images may be combined to reconstruct a full image of a tomograph of the target. The use of the data in smaller increments reduces the amount of motion artifacts that are introduced into the image and may produce an improved reconstruction tomograph of the patient. Such a method further improves the time resolution of the scanner while maintaining the radiation dosage and time of the scan.

In one aspect, the present invention provides a method of reconstructing a computed tomography image slice. The method comprises sequentially in time obtaining a plurality of attenuation data sets of a target. Limited angle reconstructions of the target are performed using at least pairs of segments of the attenuation data sets that substantially correspond in time from the plurality of attenuation data sets to create a plurality of individual interim images. The individual interim images are combined to create a full image of a slice of the target.

The sequentially obtained attenuation data sets of the target may be obtained with at least a first x-ray tube and a second x-ray tube. The first x-ray tube may define an imaging axis and the second x-ray tube may also define an imaging axis. The imaging axes of the first x-ray tube and second x-ray tubes may be positioned in a non-parallel configuration, and typically in a substantially orthogonal configuration. The first x-ray tube and the second x-ray tube may be moved at least 180 degrees around the target to obtain the plurality of attenuation data sets for the full image reconstruction of a slice of the target.

Performing the limited angle reconstructions of the sequential segments may comprise combining a segment from the first x-ray tube with a segment from the second x-ray tube that corresponds in time to the segment from the first x-ray tube. If desired, each of the segments of the attenuation data sets may be time marked. During the combining the interim images, each of the images are typically aligned in three dimensions. The x, y, z, and angular displacements needed to align each of the individual interim images with each other is recorded and the attenuation rays that correspond to the interim images are displaced the same amount as the recorded x, y, z and angular displacements. The displaced and/or rotated attenuation rays of each of the N interim images may be combined to create a set of attenuation rays for reconstruction of a full image of a slice of the target.

In some embodiments, combining comprises aligning components of the individual interim images within a volume of interest and separately summing the aligned components to create a full image of a slice of the target. In one embodiment aligning and summing the individual interim images comprises lining up the individual interim images in three dimensions within a volume of interest. A set of attenuation rays are created for each of the individual interim images and the individual sets of attenuation rays are combined and reconstructed to create a full image reconstruction of a slice of the target. Alternatively, the aligned images can be summed. In such cases, care must be taken that the individual limited angle reconstructions do not truncate the interim results.

In another aspect, the present invention provides a CT scanner that includes a first x-ray tube and a second x-ray tube. At least one x-ray detector is positioned to detect radiation emitted from the first x-ray tube and the second x-ray tube. A control system is configured to receive image information from the at least one x-ray detector. The control system may comprise means for simultaneously obtaining a plurality of attenuation data sets of a target, means for segmenting each of the attenuation data sets into individual time-sequential segments, means for performing a plurality of limited angle reconstructions using pairs of the individual segments that substantially correspond in time from the plurality of attenuation data sets to create individual interim images, and means for aligning and summing the individual interim images to create a full image reconstruction of a slice of the target.

The CT scanner may include at least one gantry for supporting and moving the first x-ray tube and the second x-ray tube. An imaging axis of the first x-ray tube and second x-ray tube are typically positioned in a non-parallel orientation, and are preferably substantially orthogonal.

In some embodiments, the control system is adapted to correct for distortions between the partial reconstruction images. The control system may also be configured to time mark each of the partial reconstruction images.

In another aspect, the present invention provides a system for reconstructing a computed tomography image slice. The system comprises a memory coupled to a processor. The memory is configured to store a plurality of code modules for execution by the processor. The plurality of code modules comprise a code module for simultaneously obtaining a plurality of attenuation data sets of a target, a code module for segmenting each of the attenuation data sets into sequential segments, a code module for performing limited angle reconstructions of the target using pairs of segments that substantially correspond in time from the plurality of attenuation data sets to create individual interim images, and a code module for aligning and summing the individual interim images to create a full image reconstruction image slice of the target.

In one embodiment, the system includes a first x-ray tube, a second x-ray tube, and at least one detector array. The x-ray tubes and detector may be configured to obtain the attenuation datasets of the target. An imaging axis of the first x-ray tube and second x-ray tube are typically positioned in a non-parallel orientation, and preferably in a substantially orthogonal position and in such a way that the beams do not overlap at the location of the detector.

In another aspect, the present invention provides a computer program stored on a computer-readable storage medium for reconstructing a computed tomography image slice. The computer program comprises code for simultaneously obtaining a plurality of attenuation data sets of a target, code for segmenting each of the attenuation data sets into sequential segments, code for performing limited angle reconstructions of the target using pairs of segments that substantially correspond in time from the plurality of attenuation data sets to create individual interim images, and code for aligning and summing the individual interim images to create a full image reconstruction image slice of the target.

In another aspect, the present invention provides an electron beam scanner. The electron beam scanner comprises a detector arc and a target arc that generates an x-ray beam that is scanned across a patient in response to an electron beam that is scanned across the target arc. A control system is configured to generate a full reconstruction image based on the information obtained by the detector arc and target arc. The control system comprises means for sequentially scanning an electron beam x-ray tube across a target from 2N different segments of an arc, wherein a set of attenuation data is obtained for each of the 2N segments, means for performing N separate limited angle reconstructions to generate N interim images, wherein each limited angle reconstruction utilizes attenuation data from at least two time-sequentially scanned segments of the arc, and means for aligning and summing the N interim images to create a full image reconstruction of a slice of the target.

A first segment of an arc may be spaced approximately ninety degrees away from a second segment of the arc. A third segment of the arc may be spaced approximately forty five degrees from at least one of the first segment and second segment. A fourth segment of the arc may be approximately ninety degrees from the third segment. As can be appreciated, in other embodiments, the spacing of the segments of the arc may be in a different pattern and may have different angular spacings.

In some embodiments, the electron beam scanner may include an electron beam steering mechanism that comprises low inductance coils. Low inductance coils are preferred since the low inductance coils improve the "jumping" ability of the electron beam between the various segments on the arc. The steering coils that are used to direct the electron beam require a finite time to reach the desired electrical current level. Therefore, each jump includes a waiting time during which the electron beam is not active. This waiting time adds to the total scanning time. It is desirable to minimize waiting time by using low inductance steering coils. In other embodiments, however, the electron beam steering mechanism may comprise conventional coils.

In a further aspect, the present invention provides a method of reconstructing a computed tomography image slice. The method comprises time-sequentially scanning an electron beam across a target generating 2N different segments of an arc, wherein a set of attenuation data is obtained for each of the 2N segments. N separate limited angle reconstructions of the target are performed to generate N interim images, wherein each limited angle reconstruction utilizes attenuation data from at least two time-sequentially scanned segments of the arc. The N interim images are aligned and summed to create a full image reconstruction image slice of the target.

In some embodiments, sequentially scanning the electron beam comprises directing the electron beam at a first segment and sweeping the electron beam through the first segment to accumulate a first attenuation data set. Thereafter, the electron beam is directed at a second segment that is approximately ninety degrees from the first segment and the electron beam is swept through the second segment to accumulate a second attenuation data set. The first of N separate limited angle reconstructions may use the first attenuation data set and second attenuation data set to generate a first interim image.

After scanning the first segment and second segment the electron beam can thereafter be directed at a third segment and swept through the third segment to accumulate a third attenuation data set. The third segment is typically approximately forty-five degrees from at least one of the first segment and second segment. The electron beam may then be directed at a fourth segment that is approximately ninety degrees from the third segment and the electron beam may be swept through the fourth segment to accumulate a fourth attenuation data set. The second of N separate limited angle reconstructions may be performed using the third attenuation data set and fourth attenuation data sets to generate a second interim image.

The aligning and summing of the interim image typically includes lining up the interim images in three dimensions. The x, y, z, and angular displacements needed to line up each of the N interim images with each other are recorded and the attenuation rays that correspond to the interim images are displaced the same amount as the recorded x, y, z, and angular displacements, such that the full reconstruction image slice comprises all of the displaced attenuation rays.

In a further aspect, the present invention provides a system for reconstructing a computed tomography image slice. The system includes a memory coupled to a processor. The memory is configured to store a plurality of code modules for execution by the processor. The plurality of code modules comprises a code module for time-sequentially scanning an electron beam across a target from 2N different segments of an arc, wherein a set of attenuation data is obtained for each of the 2N segments, a code module for performing N separate limited angle reconstructions to generate N interim images, wherein each limited angle reconstruction utilizes attenuation data from at least two time-sequentially scanned segments of the arc, and a code module for aligning and summing the N interim images to create a full image reconstruction of a slice of the target.

In another aspect, the present invention provides a computer program stored on a computer-readable storage medium for reconstructing a computed tomography image slice. The computer program comprises code for time-sequentially scanning an electron beam across a target from 2N different segments of an arc, wherein a set of attenuation data is obtained for each of the 2N segments, code for performing N separate limited angle reconstructions to generate N interim images, wherein each limited angle reconstruction utilizes attenuation data from at least two time-sequentially scanned segments of the arc, and code for aligning and summing the N interim images to create a full image reconstruction of a slice of the target.

These and other aspects will be apparent in the remainder of the figures, description and claims.

DETAILED DESCRIPTION OF THE INVENTION

The present invention generally provides imaging scanners, such as CT scanners and EBT scanners that have an improved time resolution.

Embodiments of the present invention may comprise a CT scanner that includes a plurality of x-ray sources and one or more x-ray detectors that are positioned on a gantry in different angular orientations relative to the patient. Each of the x-ray sources and detectors may simultaneous image the patient from a different angular orientation. Embodiments of the present invention may perform a limited angle reconstruction such that data obtained during only a small portion of its travel (e.g., 1/Nth of its cycle) is used to generate interim images that are obtained in short intervals in time. These individually obtained short-interval images may be combined to generate a full reconstruction tomography of the patient.

Other embodiments of the present invention comprise an EBT scanner that jumps the electron beam between points on its imaging arc that have a desired angular spacing such that the EBT scanner obtains attenuation data of the patient from different angles. Embodiments of the present invention may perform a limited angle reconstruction such that data obtained during adjacent scans in time and angularly spaced at a desired spacing (e.g., 90 degrees from each other) are used to generate interim images. The nearly simultaneously obtained images may thereafter be combined to generate a full reconstruction tomography of the patient.

Figure 1:
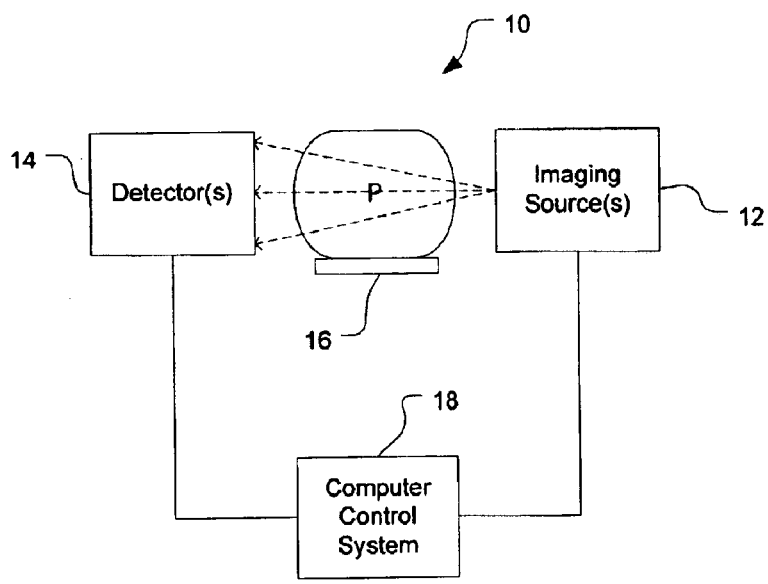
FIG. 1 schematically illustrates a simplified system of the present invention.

It should be appreciated however, that while the invention described herein focuses on the use of X-ray-based computed tomography, the present invention may also be applicable to planar nuclear medicine and SPECT imaging, and to other imaging methods where the motion of a detector is necessary, FIG. 1 illustrates a simplified imaging system 10 that is encompassed by the present invention. Imaging system 10 includes one or more movable or stationary imaging sources 12 (e.g., x-ray sources, electron beam arc, etc.) and one or more movable or stationary detector(s) or detector array 14 (e.g., x-ray detectors). In some embodiments, the sources 12 and/or detectors 14 may be mounted on a rotatable gantry (not shown) so as to rotate source(s) 12 and/or detector(s) 14 around the patient. A patient P may be positioned in a supine position on a movable or stationary support bed 16 between source(s) 12 and detector(s) 14. While not shown, as is known in the art, imaging system 10 may include rotation assemblies for rotating x-ray sources 12 and/or detector array 14 (around a Z-axis that is parallel to the patient). Moreover, in some embodiments, a drive assembly may be coupled to support bed 16 to longitudinally move the support bed along the Z-axis.

Source(s) 12 generally generate a fan beam geometry x-ray beam that is directed through the patient P and is detected by x-ray detector(s) 14 that are positioned opposite of source 12. Other alternative sources may generate a series of parallel rays. A computer control system 18 is coupled to the components of the system and controls inter alia the delivery of x-ray beams from source(s) 12, detection of the x-ray beams at detector(s) 14, movement of the source(s) 12 and/or detector(s) 14, movement of bed 16, and reconstruction of the image data obtained by detector(s) 14. As can be appreciated, in other embodiments of the present invention, instead of computer control system 18 controlling the entire system, one or more separate controllers (not shown) may be incorporated into system 10 to separately control bed 16, detectors 14, sources 12, and the like.

Figure 2:
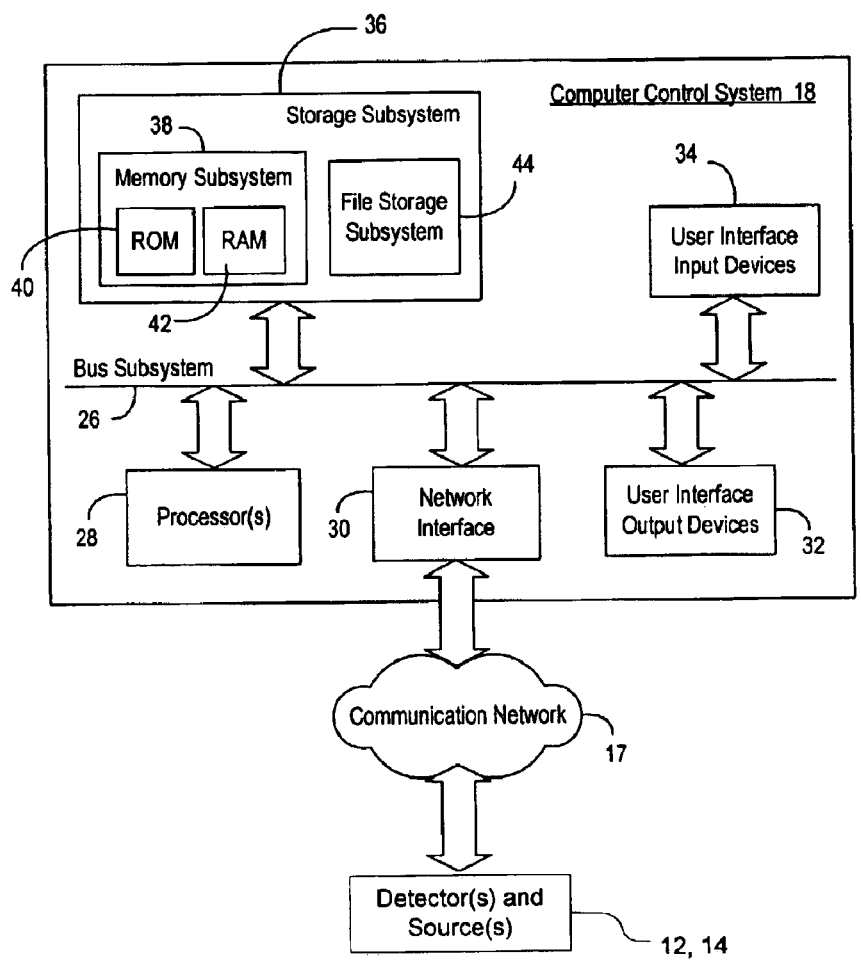
FIG. 2 schematically illustrates a simplified computer control system of the present invention.

FIG. 2 schematically illustrates one simplified computer control system 18 of the present invention. Computer control system 18 typically includes at least one processor 28 which communicates with a number of peripheral devices via a bus subsystem 26. These peripheral devices may include a storage subsystem 36, comprising a memory subsystem 38 and a file storage subsystem 44, user interface input devices 34, user interface output devices 32, and a network interface subsystem 30. Network interface subsystem 30 provides an interface to communication network 17 so as to allow for data transfer from images sources 12, detectors 14, and other outside networks.

User interface input devices 34 may include a keyboard, pointing devices such as a mouse, trackball, touch pad, or graphics tablet, a scanner, foot pedals, a joystick, a touch-screen incorporated into an output device display, audio input devices such as voice recognition systems, microphones, and other types of input devices. In general, use of the term "input device" is intended to include a variety of conventional and proprietary devices and ways to input information into computer control system 18.

User interface output devices 32 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from computer control system 18 to a user.

Storage subsystem 36 may store the basic programming and data constructs that provide the functionality of the various methods of the present invention. For example, software modules implementing the functionality of the present invention may be stored in storage subsystem 36. These software modules are generally executed by processor 28. In a distributed environment, the software modules may be stored on a plurality of computer control systems and executed by processors of the plurality of computer systems. Storage subsystem 36 typically comprises memory subsystem 38 and file storage subsystem 44. As can be appreciated, in some embodiments, the functionality of the various methods of the present invention may be carried out by hardware modules, or a combination of hardware modules and software modules.

Memory subsystem 38 typically includes a number of memories including a main random access memory (RAM) 42 for storage of instructions and data during program execution and a read only memory (ROM) 40 in which fixed instructions are stored. File storage subsystem 44 provides persistent (non-volatile) storage for program and data files, and may include computer readable medium such as a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to computer control system 18. The software modules implementing the functionality of the present invention may also be stored by file storage subsystem 44.

Bus subsystem 26 provides a mechanism for letting the various components and subsystems of computer control system 18 communicate with each other as intended. The various subsystems and components of computer control system 18 need not be at the same physical location but may be distributed at various locations within a distributed network. Although bus subsystem 26 is shown schematically as a single bus, alternate embodiments of the bus subsystem may utilize multiple busses.

Computer control system 18 itself can be of varying types including a personal computer, a portable computer, a workstation, a computer terminal, a network computer, a module in the imaging system, a mainframe, or any other data processing system. Due to the ever-changing nature of computers and networks, the description of computer control system 18 depicted in FIG. 2 is intended only as a specific example for purposes of illustrating an embodiment of the present invention. Many other configurations of computer control system 18 are possible having more or less components than the computer control system depicted in FIG. 2.

Figure 3:
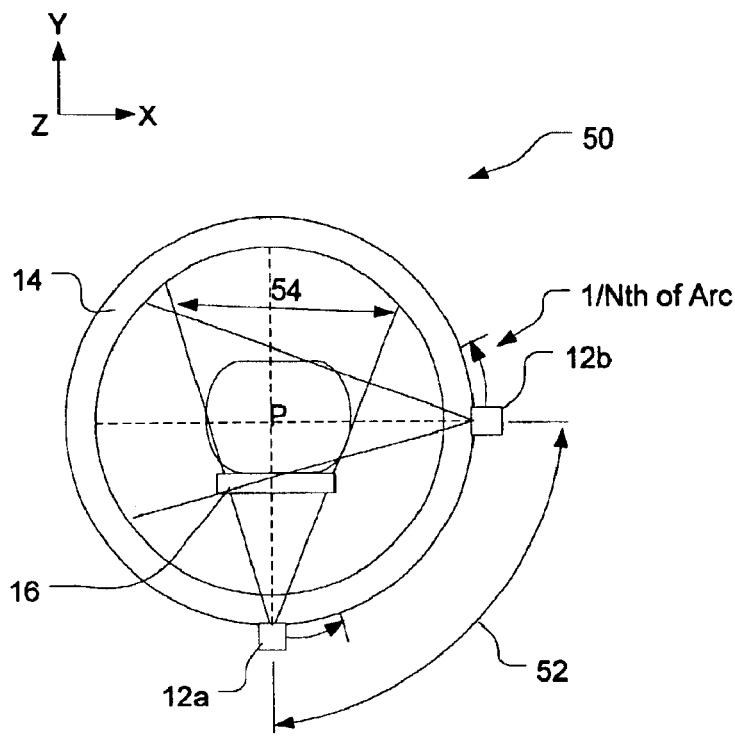
FIG. 3 schematically illustrates a simplified mechanical CT scanner of the present invention.

FIG. 3 is a simplified cross-sectional view of a mechanical CT imaging system 10 that incorporates the embodiments of the present invention. For ease of reference, only one exemplary mechanical CT scanner is illustrated, but it should be appreciated that the methods of the present invention are equally applicable to other CT scanner generations and CT scanner configurations that are not illustrated herein.

Compared to using only a very limited angle for partial angle reconstruction, if nearly-orthogonal views are obtained simultaneously, the partial angle reconstruction improves considerably. As illustrated in FIG. 3, one embodiment of imaging system is a mechanical CT scanner 50 that includes a plurality of movable x-ray sources and a stationary detector array. In one embodiment, the x-ray sources include at least a first x-ray tube 12a and a second x-ray tube 12b that are positioned on a gantry along substantially a same plane in the Z-axis direction. The first and second x-ray tubes 12a, 12b are simultaneously rotatable about the Z-axis and simultaneously produce attenuation data of the patient. A rotation assembly that is coupled to a computer control system (not shown) controls the rotation of the tubes around patient P. In the illustrated embodiment, an imaging axis (e.g., a central axis of the fan beam—shown in dotted lines) of first and second x-ray tubes 12a, 12b are angularly spaced 52 approximately ninety degrees from each other and have a fan beam angle 54 of approximately sixty degrees.

As can be appreciated, the present invention is not limited to a system that has a fan beam angle 54 of sixty degrees or an angular spacing 52 of ninety degrees from each other. For example, the first and second x-ray tube may have any desired fan beam angle 54 and may be angularly positioned in any non-parallel configuration, but should be such that the fan angles do not overlap at any one detector or any portion of a detector array. Typically, the first and second x-ray tubes are positioned anywhere between 0 degrees and 180 degrees from each other, and preferably between approximately 60 degrees and approximately 120 from each other.

While not illustrated, the mechanical scanners 50 of the present invention may include more than two x-ray tubes. For example, the mechanical scanners may include three or more x-ray tubes, if desired, so as to decrease the scanning time. Moreover, instead of a stationary detector, the present invention is also applicable to third generation CT scanners which have a movable detector array.

The computer control system of scanner 50 may be configured to perform a limited angle scan to reconstruct a tomograph of the patient. The computer control system may include software or hardware modules that are programmed to carry out the limited angle reconstruction methods of the present invention. First and second x-ray tubes 12a, 12b are typically rotated at least approximately 180 degrees around patient P who is on bed 16 to obtain a sufficient amount of attenuation data to reconstruct a tomograph image of the patient. In other embodiments, the scanners of the present invention may be configured to perform a full rotation reconstruction. Thus, first and second x-ray tubes 12a, 12b may be rotated anywhere between approximately 180 degrees and approximately 360 degrees, or more to obtain a sufficient amount of attenuation data to reconstruct a tomograph image of the patient. Some examples of methods of performing a limited angle scan are described in U.S. Pat. No. 5,053,958 to Tam, and, U.S. Pat. No. 4,138,721 to Boyd.

Figure 4:
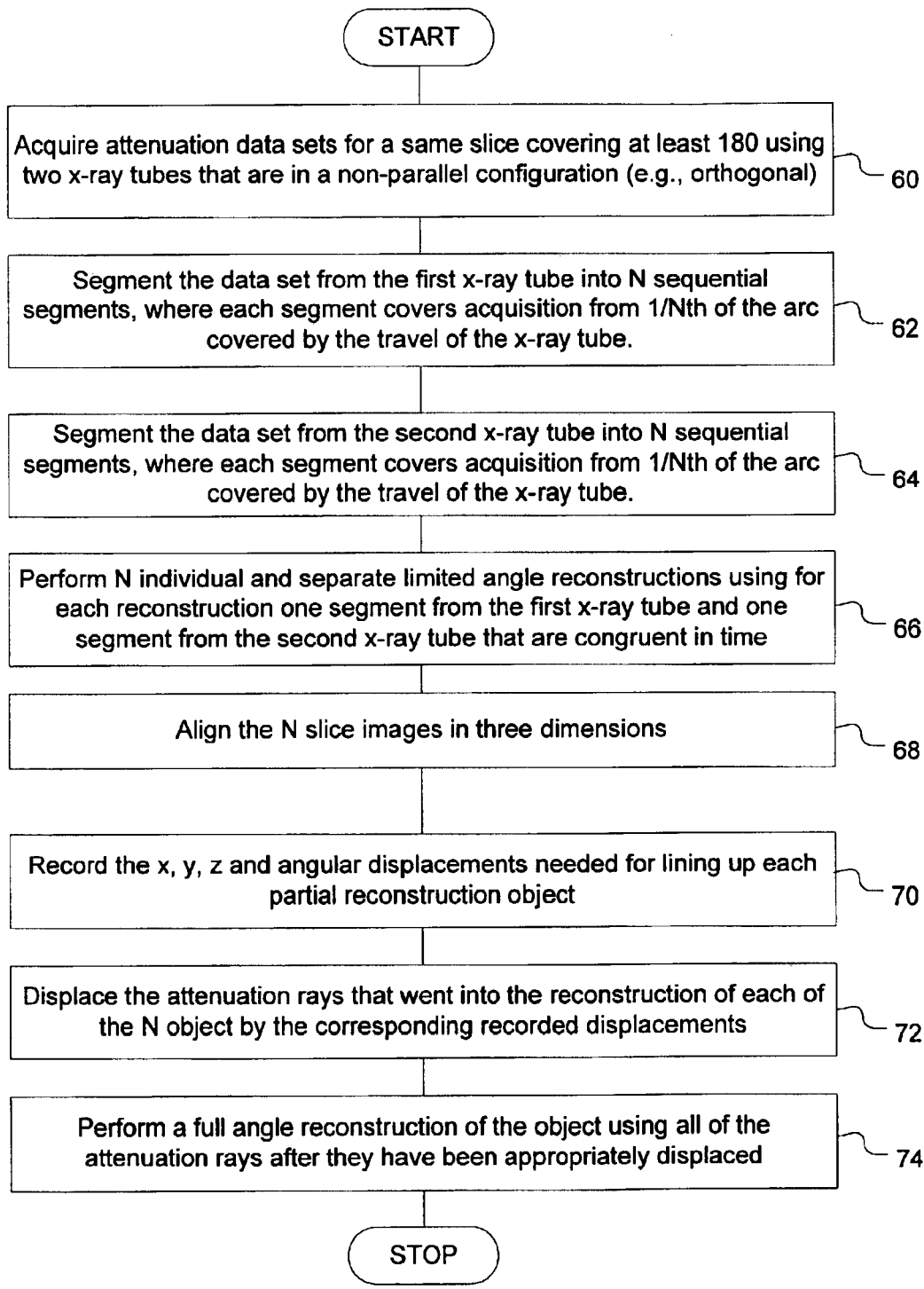
FIG. 4 schematically illustrates one simplified method of the present invention for a mechanical CT scanner of the present invention.

FIGS. 3 and 4 illustrate an embodiment of a method of the present invention that can be carried out by mechanical CT scanner 50. The x-ray tubes 12a, 12b of mechanical CT scanner 50 may be rotated around patient P in a manner similar to a conventional CT scanner. Data obtained by detectors may be delivered to the memory of the system. As noted above, a 180 degree rotation of the first and second tubes 12a, 12b will typically obtain enough data to generate a tomograph of the patient, and the time of the cycle will depend on the scanner.

In one example, illustrated in FIG. 4, first and second x-ray tubes 12a, 12b rotate at least 180 degrees around the patient to simultaneously obtain a plurality of attenuation data for a tomography image. (Step 60). Computer control system 18 may be configured to segment the each of the cycle data into a predetermined number N of individual, sequential in time segments. (Steps 62, 64).

As can be appreciated, the predetermined number N of segments may varied as desired. For example, as the number N of individual segments increase, the time resolution increases, but the signal to-noise ratio decreases and artifacts increase. Consequentially, if the segments are too fine, the interim images may not be useful.

On the other hand, if there are too few segments (e.g., too gross), there is a poorer time resolution. Advantageously, for mechanical CT scanners, the present invention allows a user to select the number N of segments after the fact, by grouping segments of attenuation data to generate the interim images.

In an EBT scanner, the methods of the present invention may be varied by combining more than 2 segments. For example a user could combine 3 or segments to generate the interim images, if desired. Since the methodology of the invention is performed after the patient has been scanned, the methods of the present invention incurs no penalty, in that there is no loss of signal-to-noise ratio or loss of resolution in the final image if an interval is chosen that is too fine. However, in an EBT there is a loss of scanning efficiency that has to do with the dead time while the beam guiding coils settle to a desired electrical current value. If the user selects too fine an interval, there is a waste of some of the time since the number of dead time intervals are increased unnecessarily One example of the present invention will now be described. A data cycle of 500 msec may be segmented into 50 segments of 10 msec each. As can be appreciated, the data cycle can be more or less than 500 msec, and will vary depending on the scanner.

A limited angle reconstruction is performed using the segmented data (e.g. 1/Nth of cycle) from one tube with the corresponding data of the other tube for each of the N individual segments to form a plurality of low resolution, limited angle reconstructions (e.g., data from Nth segment of first tube 12a is combined with data from Nth segment of second tube 12b, etc.). (Step 66).

Each of the low resolution images may be displaced and rotated so as to substantially align each of the low resolution images with each other. (Step 68). The low-resolution images are three-dimensional representations of the patient. Typically, the low resolution images may be displaced and rotated by automatic means so that they are congruent along three dimensions. The displacement and rotation of the low resolution images (and their absorption rays) may be automatically carried out by known software algorithms or other means, such as Sheehan F H et al, "Method for Three-Dimensional Data Registration From Disperate Imaging Modalities in the NOGA Myocardial Viability Trial," *IEEE Trans Medical Imaging* Vol. 21, No. 10, October 2002, pages 1264–1270, T L Faber, R W McColl, R M Opperman, J R Corbett, and R M Peshock, "Spatial and Temporal Registration of Cardiac SPECT and MR Images: Methods and Evaluation," *Radiology* 1991 179: 857–861.

In addition to displacement and rotation of the low resolution images, if needed, a morphing algorithm may be used to correct for large or small scale deformations of the object. Some non-limiting example of one morphing algorithm that may be applicable is described in Rueckert D, Sonoda L I, Hayes C, Hill D L, Leach M O, Hawkes D J, "Nonrigid Registration Using Free-Form Deformations: Application to Breast MR Images," *IEEE Trans Med Imaging* 1999, Aug; 18(8):712–21; Denton E R, Sonoda L I, Rueckert D, Rankin S C, Hayes C, Leach M O, Hill D L, Hawkes D J, "Comparison and Evaluation of Rigid, Affine, and Nonrigid Registration of Breast MR Images," *J Comput Assist Tomogr* 1999 Sep.–Oct.;23(5): 800–5. As can be appreciated, a variety of other morphing algorithms may be used to register the low-resolution images with each other.

The amount of rotation and displacement needed to align each of the low resolution images is recorded (Step 70), and the attenuation rays that correspond to each of the low resolutions images are rotated and displaced the same amount. (Step 72). This process is repeated for each of the absorption rays for each of the individual segments of the cycle. If the low resolution images have been non-rigidly displaced (e.g., morphed), new absorption rays for that segment may be calculated and used for reconstruction.

The rotated and displaced absorption rays for all of the segments for each of the x-ray tubes may then be combined to effect a reconstruction of the tomography image. (Step 74). The effective time resolution for the image will be the time length of the segment (e.g., 10 msec).

Figure 5:
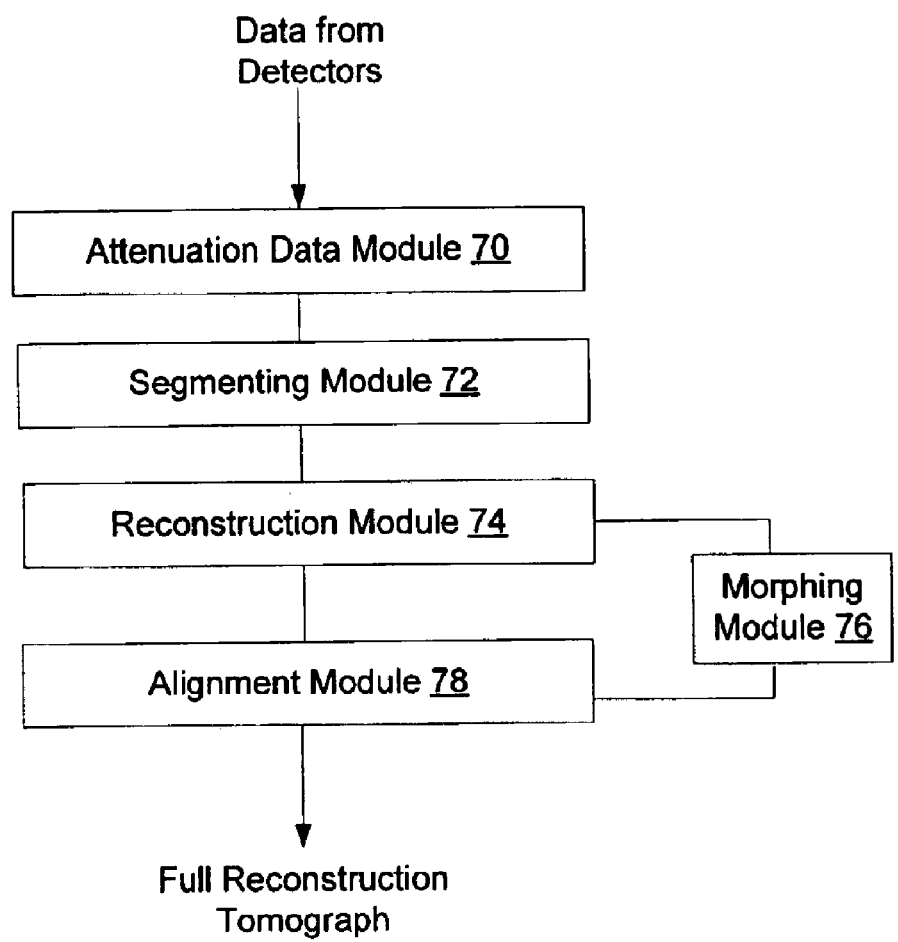
FIG. 5 schematically illustrates one simplified embodiment of modules that may be used with the CT scanners of the present invention.

FIG. 5 schematically illustrates one example of some modules that may be used in computer control system 18 with the first and second x-ray tubes 12a, 12b to reconstruct the plurality of attenuation data obtained by the tubes. The modules may be software modules, hardware modules, or a combination thereof. The modules depicted in the figures and describe herein are merely illustrative of an embodiment of the present invention and are not meant to limit the scope of the present invention as recited in the claims. One of ordinary skill in the art would recognize other variations, modifications, and alternatives.

In one embodiment, the modules are software modules that are stored in a memory of computer control system 18 and are executed by processor 28 (FIG. 2). The software modules may be embodied as a computer program that is stored on a computer-readable storage medium, such as a memory in computer control system 18.

As illustrated in FIG. 5, the first and second x-ray tubes 12a, 12b obtain a plurality of attenuation data sets of the patient, as described above. The attenuation data sets are transmitted to attenuation data module 70. While not illustrated, there may be separate attenuation data modules for receiving each of attenuation data sets, but for simplicity a single attenuation data module 70 is illustrated. The attenuation data may then be sent to a segmentation module 72 where each of the attenuation data sets are segmented into N individual segments. If desired, segmentation module may time mark each of the N individual segments so as to make it improve the matching of the corresponding segments of each of the attenuation data sets. Once the attenuation data sets are segmented, the data sets are sent to reconstruction module 74 where the attenuation data sets may be reconstructed to form N interim images, as described above.

The N individual interim images may be transmitted to alignment module 78, wherein the interim images are combined. Alignment module 78 may combine the interim images by displacing and/or rotating the images so as to line up the individual images in three dimensions. If needed the interim images are transmitted to a morphing module 76, where morphing module may correct any large scale deformations (or other deformations) between the individual interim images and may re-calculate the absorption rays for any image that has been non-rigidly displaced (e.g., "morphed").

Alignment module 78 performs a corresponding displacement and/or rotation to the absorption rays that correspond with the displacement and/or rotation of the interim images. Thereafter, the displaced and/or rotated absorption rays for each of the segments are combined so as to generate a full reconstruction image of the patient, as is describe in detail above.

Figure 6:
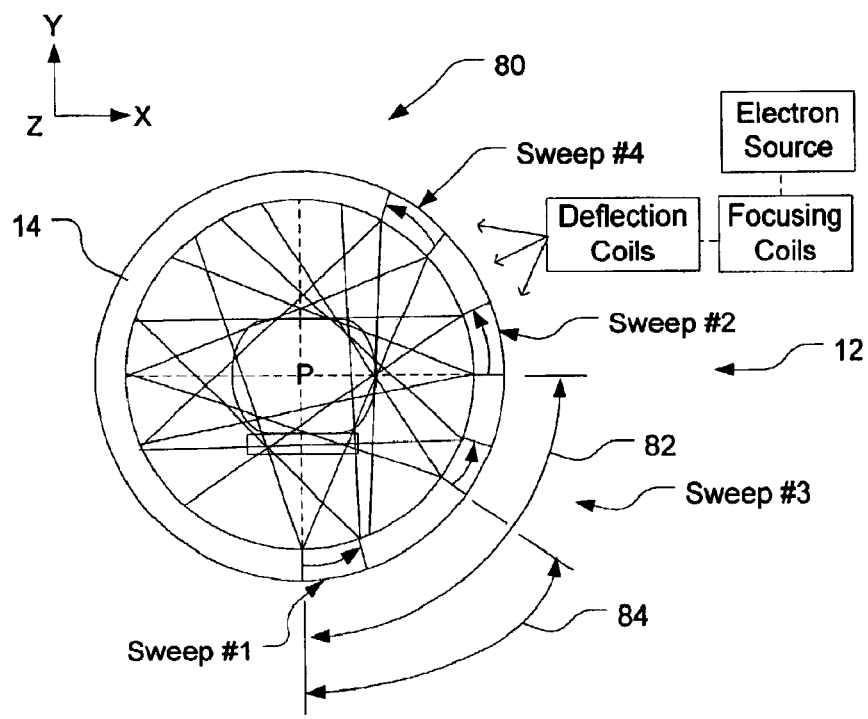
FIG. 6 schematically illustrates a simplified EBT scanner of the present invention.

In another embodiment of the present invention illustrated in FIG. 6, the imaging systems of the present invention incorporate an electron beam scanner 80. As is known in the art, electron beam scanners 80 make use of an electron source, focusing coils, and a deflection coil to direct a beam of electrons that produce x-rays that are scanned or directed across a target patient P from one or more arcs of tungsten target rings 12 that encircle at least a portion of patient P. The electron beam is electronically steered across a target that emits x-rays from the beam location, so that the x-ray beam is scanned across the patient and onto a detector ring 14 that is opposite of the arcs of tungsten so as to generate a cross sectional image of the patient.

In the illustrated embodiment, detector ring 14 of this embodiment are stationary. The electron beam may have an x-ray fan beam angle between approximately thirty degrees and approximately 90 degrees. Mathematically, the image reconstructions process for an electron bean scanner is substantially the same as for mechanical CT scanner 50, except that the beam can be scanned across patient P faster than the x-ray tube can be rotated. As such, the imaging time needed to obtain data for a single slice can be reduced, typically to a time between approximately 50 msec and 100 msec.

In some embodiments, electron beam scanner 80 may include low inductance deflection coils (or beam steering coils) to improve the settling time of the beam during the steering or "jumping" of the electron beam to the desired points on tungsten target rings.

In an EBT scanner, the electron beam may be "jumped" between points on the arc that are separated by a first desired angular separation 82 so as to obtain data for a tomograph image. Data from two or more sequential (in time) segment sweeps may be combined to generate an interim image of patient P. Subsequent "jumps" may be made around the first and second segments until all of the desired segments 2N of the target arc have been swept. In the illustrated embodiment, the first desired angular separation 82 is approximately 90 degrees from the next segment. As can be appreciated, any desired first angular separation 82 between 0 degrees and approximately 180 degrees may be used between sequential jumps.

Once the desired segments of the arc have been swept, segments that are taken sequentially in time and that are spaced in the desired angular separation (e.g., 90 degrees), are combined to create N individual interim images. Similar to the above methods, the N interim images are rotated and displaced so as to effect a full reconstruction tomography of the patient.

Figure 7:
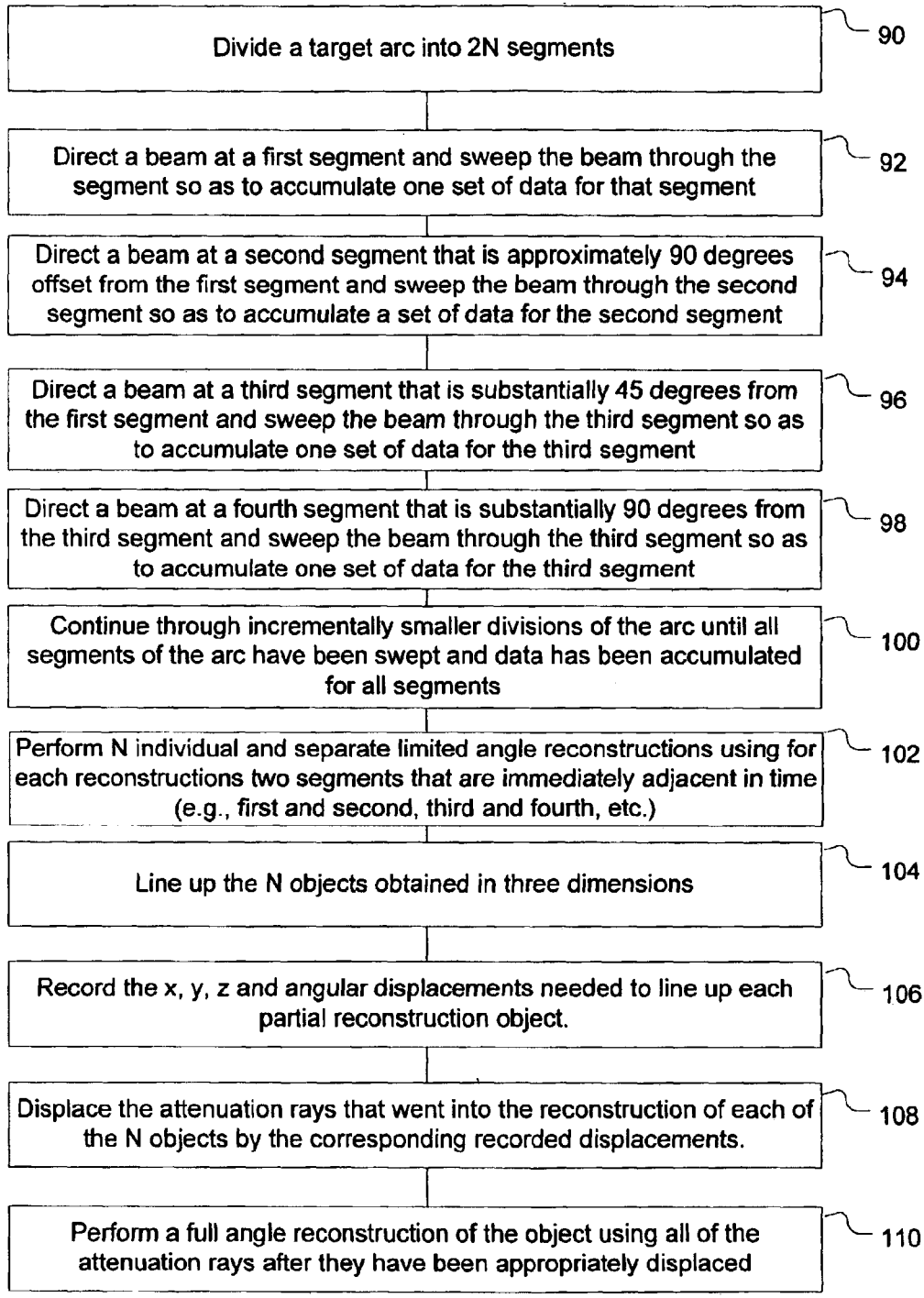
FIG. 7 schematically illustrates one simplified method of the present invention for the electron beam imaging device.

One specific method of the present invention is schematically illustrated in FIGS. 6 and 7. The target arc may first be divided into 2N segments. (Step 90). A beam is jumped to a first segment and is swept through the first segment so as to accumulate attenuation data for the first segment. (Step 92). The beam is jumped to a second segment that is angularly offset at a desired angular offset 82 (e.g., approximately 90 degrees) from the first segment. The beam is swept through the second segment so as to accumulate attenuation data for the second segment. (Step 94).

Thereafter, the beam is jumped to a third segment that is angularly offset a second desired angular spacing 84 (e.g., approximately 45 degrees) from the first segment. The electron beam is swept through the third segment so as to accumulate attenuation data for the third segment. (Step 96). As shown in FIG. 6, the third segment is approximately in a mid-point between the first segment and second segment. The beam is then jumped to a fourth segment that is angularly offset the first desired angular spacing (e.g., approximately 90 degrees) from the third segment and the electron beam is swept through the fourth segment to accumulate attenuation data for the fourth segment. (Step 98). This process is continued through incrementally smaller divisions until all of the desired segments of the arc have been swept by the beam and attenuation data has been accumulated for all of the desired segments. (Step 100). Subsequent sweep segments (e.g., fifth segment, sixth segment, and the like) may be jumped to anywhere between the first and third sweep or second and fourth sweep, respectively. As can be appreciated, a variety of jump patterns may be used to accumulate the attenuation data of the patient, and the present invention is not limited to the jump pattern, recited above. For example, instead of having an angular spacing 84 the third sweep approximately 45 degrees from the first sweep, the third sweep may be positioned more or less than 45 degrees from the first sweep.

Once the jumps and sweeps are completed, N individual and separate limited angle reconstructions are performed. In one embodiment, the limited angle reconstructions are performed using two segments that are immediately adjacent in time and which are separated by the first angular offset (e.g., first and second segments, third and fourth segments, etc.) so as to generate N interim, low resolution images. (Step 102).

The N individual interim images may then be aligned in three dimensions by displacing and/or rotating the interim images. (Step 104). If needed, as described above, the interim images may be morphed to correct for any large scale differences between the individual interim images. The amount of rotation and displacement needed to align each of the low resolution images is recorded (Step 106), and the attenuation rays that correspond to each of the low resolutions images are rotated and displaced the same amount. (Step 108). This process is repeated for each of the absorption rays for each of the segments of the cycle. If the low resolution images have been non-rigidly displaced (e.g., morphed), new absorption rays for that segment may be calculated and used for reconstruction.

The rotated and displaced absorption rays for all of the segments for each of the x-ray tubes may then be combined to effect a reconstruction of the tomography image. (Step 110). A desired time resolution of the EBT scanner may be chosen based on the dwell time of the electron beam for each segment. For example, if the electron beam dwells for 5 msec in one segment of patient P, and then dwell on the patient P for another 5 msec in a subsequent segment, then data sets with a 10 msec time resolution may be obtained.

If the signal-to-noise and/or artifact level of the two-segment interim image is not satisfactory, then three (or possibly four or more) time-consecutive segments can be used for interim image reconstruction. Because the beam is jumped maximally in sequential shots, the data of three (or four or more) segments sample as much of the total rotation arc as possible. For three segments a 15 msec time resolution may be obtained.

Figure 8:
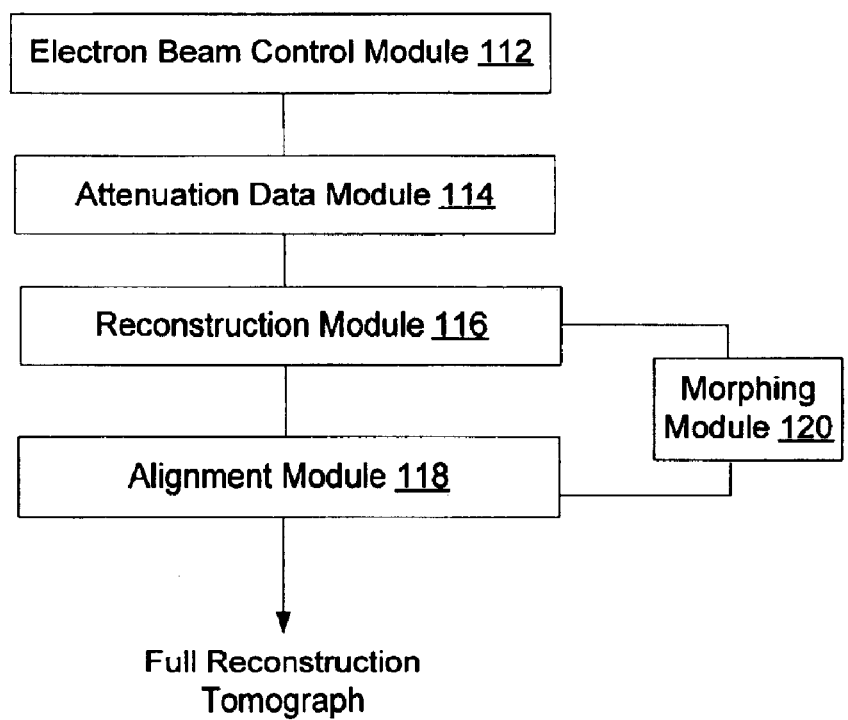
FIG. 8 schematically illustrates one simplified embodiment of modules that may be used with the EBT scanners of the present invention.

FIG. 8 schematically illustrates one example of some modules that may be used in computer control system 18 with EBT scanner 80 to reconstruct the plurality of attenuation data obtained by the electron beam and detector array. The modules may be software modules, hardware modules, or a combination thereof. The modules depicted in the figures and describe herein are merely illustrative of an embodiment of the present invention and are not meant to limit the scope of the present invention as recited in the claims. One of ordinary skill in the art would recognize other variations, modifications, and alternatives.

In one embodiment, the modules are software modules that are stored in a memory of computer control system 18 and are executed by processor 28 (FIG. 2). The software modules may be embodied as a computer program that is stored on a computer-readable storage medium, such as a memory in computer control system 18. As illustrated in FIG. 8, an electron beam control module 112 may be configured to divide a target arc of the electron beam scanner into 2N segments. The jumping of electron beam between the 2N segments on the arc to obtain an attenuation data sets is controlled with electron beam control module 112. The attenuation data sets are transmitted to attenuation data module 114, where the data is stored either as separate segments, as a time marked data set, or as a single attenuation data set. The data sets may then be sent to reconstruction module 116 where the 2N attenuation data sets may be reconstructed to form N interim images, as described above.

The N individual interim images may be transmitted to alignment module 118, wherein the interim images are combined. Alignment module 118 may combine the interim images by displacing and/or rotating the images so as to line up the images in three dimensions. If needed the interim images are transmitted to a morphing module 120, where morphing module may correct any large scale deformations between the interim images and may re-calculate the absorption rays for any image that has been non-rigidly displaced (e.g., "morphed").

Alignment module 118 performs a corresponding displacement and/or rotation to the absorption rays that correspond with the displacement and/or rotation of the interim images. Thereafter, the displaced and/or rotated absorption rays for each of the segments are combined so as to generate a full reconstruction image of the patient, as is describe in detail above.

As will understood by those of skill in the art, the present invention may be embodied in other specific forms without departing from the essential characteristics thereof. As can be appreciated, the present invention is applicable to all types of imaging scanners, no matter how fast the scanners perform. Accordingly, the foregoing description is intended to be illustrative, but not limiting, of the scope of the invention which is set forth in the following claims.

What is claimed is:

1. A method of reconstructing a computed tomography image slice, the method comprising:
   sequentially in time obtaining a plurality of attenuation data sets of a target;
   segmenting each of the attenuation data sets into time-sequential segments;
   performing limited angle reconstructions of the target using pairs of segments that substantially correspond in time from the plurality of attenuation data sets to create individual interim images; and
   combining the individual interim images to create a full image of a slice of the target.

2. The method of claim 1 wherein sequentially obtaining the attenuation data sets of the target is carried out with at least a first x-ray tube and a second x-ray tube.

3. The method of claim 2 wherein the first x-ray tube defines an imaging axis and the second x-ray tube defines an imaging axis, the method further comprising positioning the imaging axes of the first x-ray tube and second x-ray tubes in a non-parallel configuration.

4. The method of claim 3 wherein the imaging axes of the first x-ray tube and second x-ray tube are positioned in a substantially orthogonal configuration.

5. The method of claim 2 wherein the first x-ray tube and the second x-ray tube are moved at least 180 degrees around the target to obtain the plurality of attenuation data sets for the full image reconstruction of a slice of the target.

6. The method of claim 2 wherein performing limited angle reconstructions of the sequential segments comprises combining a segment from the first x-ray tube with a segment from the second x-ray tube that corresponds in time to the segment from the first x-ray tube.

7. The method of claim 6 comprising time marking each of the segments of the attenuation data sets.

8. The method of claim 1 wherein aligning comprises aligning the interim images in three dimensions.

9. The method of claim 1 wherein aligning and summing the individual interim images comprises:
   lining up the individual interim images in three dimensions;
   recording the x, y, z, and angular displacements needed to line up each of the individual interim images with each other;
   displacing attenuation rays that correspond to the interim images the same amount as the recorded x, y, z and angular displacements; and
   performing a reconstruction of the image using the combined and displaced attenuation rays.

10. The method of claim 1 wherein combining comprises aligning the components of the individual interim images and summing separately these aligned components to create a full image of a slice of the target.

11. A CT scanner comprising:
    a first x-ray tube;
    a second x-ray tube;
    at least one x-ray detector positioned to detect radiation emitted from the first x-ray tube and the second x-ray tube;
    a control system configured to receive image information from the at least one x-ray detector, wherein the control system comprises:

means for simultaneously obtaining a plurality of attenuation data sets of a target;

means for segmenting each of the attenuation data sets into time-sequential segments;

means for performing limited angle reconstructions using pairs of segments that substantially correspond in time from the plurality of attenuation data sets to create individual interim images; and means for aligning and summing the individual interim images to create a full image reconstruction of a slice of the target.

12. The system of claim 11 comprising at least one gantry for the first x-ray tube and the second x-ray tube.

13. The system of claim 12 wherein an imaging axis of the first x-ray tube and second x-ray tube are positioned in a non-parallel orientation.

14. The system of claim 13 wherein the imaging axes of the first x-ray tube and second x-ray tube are substantially orthogonal.

15. The system of claim 11 wherein the means for aligning and summing are configured to align components of the individual interim images and sum separately these aligned components to create a full image of a slice of the target.

16. The system of claim 11 wherein the control system is adapted to correct for distortions between the partial reconstruction images.

17. The system of claim 11 wherein the control system is configured to time mark each of the partial reconstruction images.

18. A system for reconstructing a computed tomography image slice comprising:

a processor;

a memory coupled to the processor, the memory configured to store a plurality of code modules for execution by the processor, the plurality of code modules comprising:

a code module for simultaneously obtaining a plurality of attenuation data sets of a target;

a code module for segmenting each of the attenuation data sets into sequential segments;

a code module for performing limited angle reconstructions of the target using pairs of segments that substantially correspond in time from the plurality of attenuation data sets to create individual interim images; and a code module for aligning and summing the individual interim images to create a full image reconstruction image slice of the target.

19. The system of claim 18 further comprising a first x-ray tube, a second x-ray tube, and at least one detector, wherein the detector is configured to obtain the attenuation datasets of the target.

20. The system of claim 19 wherein an imaging axis of the first x-ray tube and second x-ray tube are positioned in a non-parallel orientation.

21. The system of claim 20 wherein the imaging axes of the first x-ray tube and second x-ray tube are substantially orthogonal.

22. A computer program stored on a computer-readable storage medium for reconstructing a computed tomography image slice, the computer program comprising:

code for simultaneously obtaining a plurality of attenuation data sets of a target;

code for segmenting each of the attenuation data sets into sequential segments;

code for performing limited angle reconstructions of the target using pairs of segments that substantially correspond in time from the plurality of attenuation data sets to create individual interim images; and code for aligning and summing the individual interim images to create a full image reconstruction image slice of the target.

23. A method of reconstructing a computed tomography image slice, the method comprising:

time-sequentially scanning an electron beam across a target generating 2N different segments of an arc, wherein a set of attenuation data is obtained for each of the 2N segments;

performing N separate limited angle reconstructions of the target to generate N interim images, wherein each limited angle reconstruction utilizes attenuation data from at least two time-sequentially scanned segments of the arc;

aligning and summing the N interim images to create a full image reconstruction image slice of the target.

24. The method of claim 23 wherein sequentially scanning an electron beam comprises:

directing the electron beam at a first segment and sweeping the electron beam through the first segment to accumulate a first attenuation data set; and directing the electron beam at a second segment that is approximately ninety degrees from the first segment and sweeping the electron beam through the second segment to accumulate a second attenuation data set.

25. The method of claim 24 wherein performing the first of N separate limited angle reconstructions comprises using the first attenuation data set and second attenuation data set to generate a first interim image.

26. The method of claim 25 wherein sequentially scanning an electron beam further comprises:

directing the electron beam at a third segment and sweeping the electron beam through the third segment to accumulate a third attenuation data set, wherein the third segment is approximately forty-five degrees from at least one of the first segment and second segment; and directing the electron beam at a fourth segment that is approximately ninety degrees from the third segment and sweeping the electron beam through the fourth segment to accumulate a fourth attenuation data set.

27. The method of claim 26 wherein performing the second of N separate limited angle reconstructions comprises using the third attenuation data set and fourth attenuation data sets to generate a second interim image.

28. The method of claim 26 wherein the third attenuation data set and fourth attenuation data set are reconstructed to generate a second interim image.

29. The method of claim 23 wherein aligning and summing comprises lining up the interim images in three dimensions.

30. The method of claim 23 wherein aligning and summing the N interim images comprises:

recording the x, y, z, and angular displacements needed to line up each of the N interim images with each other; and displacing attenuation rays that correspond to the interim images the same amount as the recorded x, y, z, and angular displacements.

31. The method of claim 30 wherein the full reconstruction image slice comprises all of the displaced attenuation rays.

32. The method of claim 23 wherein the arc for each of the 2N segments is between 6 degrees and 60 degrees.

33. An electron beam scanner comprising:

a detector arc;

a target arc that generates an x-ray beam that is scanned across a patient; and a control system that is configured to generate a full reconstruction image, wherein the control system comprises:

means for sequentially scanning an electron beam across a target from 2N different segments of an arc, wherein a set of attenuation data is obtained for each of the 2N segments;

means for performing N separate limited angle reconstructions to generate N interim images, wherein each limited angle reconstruction utilizes attenuation data from at least two time-sequentially scanned segments of the arc;

means for aligning and summing the N interim images to create a full image reconstruction of a slice of the target.

34. The electron beam scanner of claim 33 wherein a first segment of an arc is spaced approximately ninety degrees away from a second segment of the arc.

35. The electron beam scanner of claim 33 wherein the electron beam steering mechanism comprises low inductance coils.

36. A system for reconstructing a computed tomography image slice comprising:

a processor;

a memory coupled to the processor, the memory configured to store a plurality of code modules for execution by the processor, the plurality of code modules comprising:

a code module for time-sequentially scanning an electron beam across an x-ray generating target for 2N different segments of an arc, wherein a set of attenuation data is obtained for each of the 2N segments;

a code module for performing N separate limited angle reconstructions to generate N interim images, wherein each limited angle reconstruction utilizes attenuation data from at least two time-sequentially scanned segments of the arc; and a code module for aligning and summing the N interim images to create a full image reconstruction of a slice of the target.

37. A computer program stored on a computer-readable storage medium for reconstructing a computed tomography image slice, the computer program comprising:

code for time-sequentially scanning an electron beam across an x-ray generating target for 2N different segments of an arc, wherein a set of attenuation data is obtained for each of the 2N segments;

code for performing N separate limited angle reconstructions to generate N interim images, wherein each limited angle reconstruction utilizes attenuation data from at least two time-sequentially scanned segments of the arc; and code for aligning and summing the N interim images to create a full image reconstruction of a slice of the target.

38. The method of claim 1 wherein aligning and summing the N interim images comprises:

within a volume of interest lining up the N interim images in three dimensions;

creating a set of attenuation rays for each of the N interim images;

combining the N sets of attenuation rays; and reconstructing the combined set of attenuation rays to create a full image reconstruction of a slice of the target.

39. The method of claim 1 wherein combining comprises aligning components of the N interim images and summing separately these aligned components to create a full image of a slice of the target.

\* \* \* \* \*